United States Patent [19]

Upton

[11] Patent Number: 5,031,641

[45] Date of Patent: Jul. 16, 1991

[54] HAND RESTRAINT FOR HANDCUFFS

[76] Inventor: Michael Upton, 1220 Thompson Pl., Daytona Beach, Fla. 32118

[21] Appl. No.: 569,197

[22] Filed: Aug. 20, 1990

[51] Int. Cl.⁵ .................................................. A61F 5/37
[52] U.S. Cl. .................................... 128/879; 128/878; 150/101; 70/16; 70/18
[58] Field of Search ............... 128/869, 873, 877, 878, 128/879; 70/14, 15, 16, 17, 18; 150/100, 101, 102, 103, 150

[56] References Cited

U.S. PATENT DOCUMENTS

| | | | |
|---|---|---|---|
| 2,188,787 | 1/1940 | Keener | 128/879 |
| 2,949,761 | 4/1960 | Mitchell et al. | 128/879 |
| 3,176,683 | 4/1965 | Posey | 128/879 |
| 4,469,096 | 9/1984 | Rivadeneyra | 128/879 |

FOREIGN PATENT DOCUMENTS 1532866  9/1966  Fed. Rep. of Germany ...... 150/102

Primary Examiner—Mickey Yu
Assistant Examiner—David J. Kenealy
Attorney, Agent, or Firm—Macdonald J. Wiggins

[57] ABSTRACT

A restraint for the hands of a handcuffed person includes a fabric pouch having a drawstring, and grommets along an edge thereof. The drawstring has a ring at one portion, and a spring clip at an opposing portion. The pouch is placed over both hands of a handcuffed person, the drawstring pulled tight by means of the spring clip which is passed through the ring and attached to a grommet. A plastic liner may be installed in the pouch prior to use to protect and collect evidence from a suspect's hands.

14 Claims, 1 Drawing Sheet

HAND RESTRAINT FOR HANDCUFFS

BACKGROUND OF THE INVENTION

1. Field of the Invention

The present invention relates to handcuffs, and more particularly to a cover, restraint and evidence protector for the hands of a handcuffed person.

2. Description of the Prior Art

Handcuffs are used to control prisoners or others at arrest, during transfer, and similar circumstances. Although such use may limit the handcuffed person's arms, his hands are still free. Cases of a handcuffed prisoner gaining access to weapons are known, as well as escape from vehicles by opening doors. Also, a prisoner may have incriminating evidence on his hands which can be lost during transport.

One attempt in the prior art to provide protection from a prisoner's hands is shown in Bible U.S. Pat. No. 4,741,051. A protective mitt is placed over the handcuffed hands, and attached by a tie wrap which must be threaded through four small holes in the mitt. The disadvantages of the Bible device is that the mitt is not completely closed, and difficulty may be experienced in threading the tie wrap with an uncooperative prisoner. A shackle formed from two separate mitts is taught by James U.S. Patent No. 404,544. McKenzie U.S. Pat. No. 1,529,546, discloses a rigid mitt that holds a prisoner's hands palm to palm, with each thumb separated and relatively immobile.

There is a need for a simple, compact cover and restraint that may be carried by an officer, which can be quickly installed, and which includes means for protecting evidence on the hands.

SUMMARY OF THE INVENTION

The present invention is a pouch formed of a strong fabric, and having a hem around the open end thereof. The hem has a pair of diametrically opposed openings, and a drawstring threaded therethrough. The drawstring extends through the hem at each opening. A spring clip is attached to one end of the drawstring, and a ring through which the spring clip can pass is attached to the other end of the drawstring.

One or more grommets are placed along a lower portion of the pouch. A removable, disposable plastic liner is provided having a suitable closure that is placed in the pouch prior to use. To use the restraint, the person is handcuffed normally. The pouch is fully opened, and the person's hands placed into the pouch. The spring clip and ring are grasped, and pulled apart to tighten the open end of the pouch around the person's wrists. Next, the spring clip is passed between the person's arms, and through the ring. The spring clip is then clipped to one of the grommets. The use of several grommets permits selection of one that will maintain the pouch tightly closed around the person's wrists.

As will be recognized, the plastic liner will capture or protect any evidence on a prisoner's hand, such as drugs, blood, and the like; and prevents the prisoner from getting rid of evidence on the hands or beneath fingernails. The pouch serves to prevent a prisoner from any overt acts using the hands, and permits several prisoners to be handled together without danger of cooperative acts. A person may be handcuffed with hands in front or back using the invention. The invention also prevents a prisoner from breaking, or attempting to break, the handcuffs. The invention also provides a psychological deterrent to a prisoner's attempt to escape.

When the pouch is removed at a police station, or the like, the plastic liner may be removed, closed, and marked with a felt pen. The liner may be later analyzed for any possible evidence.

It is therefore a principal object of the invention to provide a restraint for the hands of a handcuffed person using a pouch, a drawstring, and means for tightening and securing the pouch around the person's wrists.

It is another object of the invention to provide a restraining pouch for covering a handcuffed person's hands having a plastic liner for collecting and protecting any evidence from or on the person's hands.

It is still another object of the invention to provide a restraint that covers the hands of a handcuffed person with a strong fabric cloth, and a drawstring that is passed between the person's arms and secured to the pouch.

It is yet another object of the invention to provide a prisoner hand restraint for preventing the prisoner from using his hands to access weapons, destroy or lose evidence, or to escape.

These and other objects and advantages will become apparent from the following detailed description when read in conjunction with the drawings.

DETAILED DESCRIPTION OF THE PREFERRED EMBODIMENT

Figure 1:
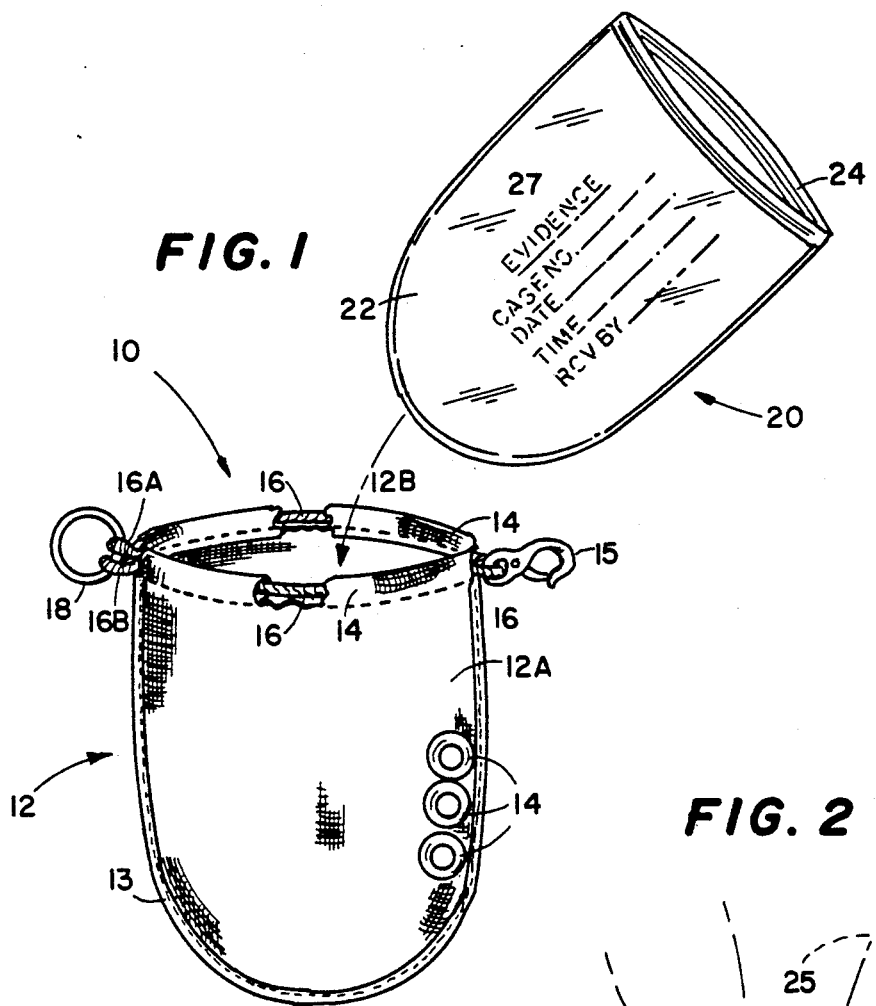
FIG. 1 is a perspective view of the hand restraint of the pouch of the invention, and a disposable plastic liner.

Referring to FIG. 1, a perspective view of the hand restraint 10 of the invention is shown. A pouch 12 is fabricated from a strong fabric, such as canvas, nylon, or the like. A seam 13 defines a right side 12A and a left side 12B. A hem 14 is provided for each side, 12A and 12B. Each hem 14 is open at its end. A drawstring 16, as shown in the cutaway portions of hems 14, is threaded through the hems 14. Any strong cord, such as nylon, flexible metallic cable, or the like, may be used. The free ends of drawstring 16A and 16B may be attached to a steel ring 18, and the portion projecting through the other hem opening may be passed through the eye of a spring clip 15. The size of ring 18 is selected to permit spring clip 15 to be passed therethrough.

Three grommets are shown adjacent the portion of seam 13 nearest spring clip 15. A liner 20, formed of plastic or other suitable material, is shown that may be installed in restraint 10 as indicated by the arrow. Liner 20 includes a body 22 and a closure 24. A label 27 on body 22 permits the identification of any evidence contained therein to be preserved. A new liner 20 is installed in restraint 10 after each use. After use of restraint 10, liner 20 is removed and may be analyzed for any residues or evidence from a suspect's hands. As will be recognized, liner 20 also prevents contamination by outside sources of evidence on a suspect's hands.

Figure 2:
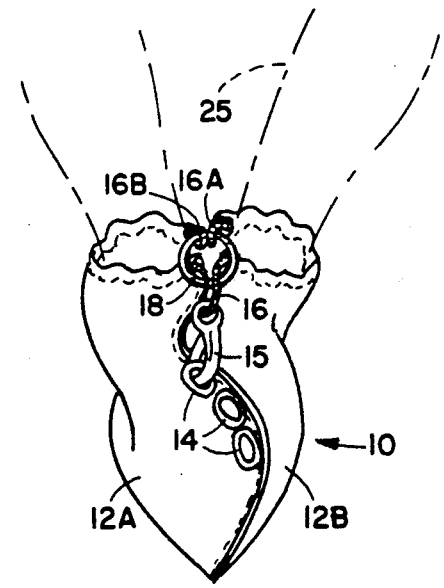
FIG. 2 is a perspective view of the hand restraint in place over a handcuffed person's hands.
Figure 3:
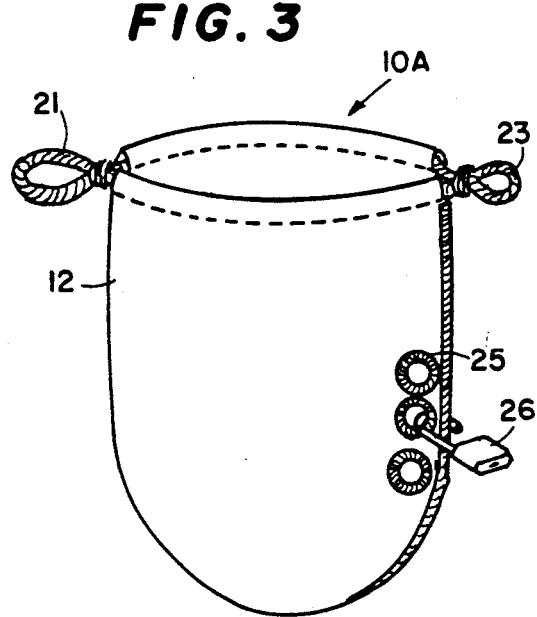
FIG. 3 is a perspective view of an alternative embodiment of the invention.

Turning now to FIG. 2, restraint 10 is shown installed on a pair of handcuffed hands and wrists of arms 25 shown in phantom view. The pouch 12 is placed over the hands with side 12A to the left and side 12B to the right. This places spring clip 15 at the front and ring 18 at the rear. The officer grasps ring 18 in one hand and spring clip 15 in the other to tighten drawstring 16 as tight as possible about the wrists. The spring clip is passed through ring 18, as shown, and clipped to a grommet 14 that will maintain the desired tightness of pouch 10 around the wrists. As will be noted, drawstring 16 passes over the connecting chain of the two handcuffs (not shown), thereby preventing the restraint 10 from being removed without releasing spring clip 15. Although the preferred implementation of the invention utilizes ring 18, spring clip 15, and grommets 14, other means may be used with the same utility. FIG. 3 presents an alternative arrangement. A first loop 21 may be sewn in drawstring 16 to replace ring 18, and a second loop 23 may replace spring clip 15. Holes 25 are punched through pouch 12, and reinforced by stitching in place of grommets 14. Second loop 23 is threaded through first loop 21 and attached to a hole 14 by a small padlock 26. This alternative embodiment has the advantage that the restraint 10A can only be removed by a person with the key to padlock 26.

It will now be recognized that the invention provides a restraint for a handcuffed person that is quickly installed and removed. The restraint protects and retains any evidence from the person's hands, and prevents overt acts of the person toward escape or injury of the officer. The device is compact, and can folded into a small package for carrying by an officer.

Although a particular implementation of the invention has been disclosed for exemplary purposes, various changes in materials, shape, and construction details may be made, such changes are considered to fall within the spirit and scope of the invention.

I claim:

1. A restraint for the hands of handcuffed persons comprising:
   a fabric pouch;
   a hem around an open end of said pouch, said hem including a pair of diametrically opposed openings;
   a drawstring inserted through said hem and having a first end extending through one of said openings, and a second end extending through the other of said openings;
   fastening means attached to said first end of said drawstring;
   a ring attached to said second end of said drawstring; and
   at least one grommet through a lower wall of said pouch.

2. The restraint as defined in claim 1 in which said fastening means is a spring clip.

3. The restraint as defined in claim 1 in which said pouch is formed from canvas.

4. The restraint as defined in claim 3 in which said pouch is formed from nylon fabric.

5. The restraint as defined in claim 3 in which the length of said drawstring is selected to permit said spring clip to be passed through said ring, when said pouch is covering the hands of a handcuffed person, and said spring clip attached to said grommet to thereby close said open end around wrists of said person.

6. The restraint as defined in claim 1 which further comprises a disposable plastic liner for insertion into said pouch for preserving evidence in or on hands of a handcuffed person.

7. A restraint for covering the hands and handcuffs of a handcuffed person, said handcuffs connected by a chain, comprising:
   a pouch formed of a strong fabric, said pouch having an open end, and a seam extending downwardly from said open end;
   drawstring means disposed around said open end for closing said pouch, said means including a first drawstring end, and a second drawstring end which may be passed through said first end for closing said pouch;
   said pouch having at least one hole through a lower wall thereof, adjacent said seam for attaching said first end after closing of said pouch; and
   means for attaching said second end to said hole;
   whereby said pouch is placed over the handcuffed hands, said first drawstring end is passed over said handcuff connecting chain, through said second end, and attached to said hole, thereby captivating said restraint.

8. The restraint as defined in claim 7 in which said attaching means is a spring clip attached to said first drawstring end.

9. The restraint as defined in claim 8 which further comprises a ring attached to said second drawstring end for passing said spring clip and first end therethrough.

10. The restraint as defined in claim 7 in which said attaching means is a padlock.

11. The restraint as defined in claim 7 which further comprises a disposable plastic liner for insertion into said pouch for preserving evidence in or on hands of a handcuffed person.

12. The restraint as defined in claim 7 in which:
    said drawstring means includes a hem around said open end of said pouch;
    said hem including a pair of diametrically opposed openings;
    a cord threaded through said hem and projecting from said openings;
    a spring clip attached to said cord projecting from one of said openings; and
    a ring attached to said cord projecting from the other of said openings.

13. The restraint as defined in claim 7 in which said hole is formed by a grommet.

14. The restraint as defined in claim 12 which a plurality of grommets is disposed along said seam to provided adjustment of closure of said open end of said pouch.

* * * * *